United States Patent
Luginbuehl et al.

(10) Patent No.: US 8,206,457 B2
(45) Date of Patent: Jun. 26, 2012

(54) PROSTHETIC DEVICE FOR CARTILAGE REPAIR

(75) Inventors: Reto Luginbuehl, Bettlach (CH); Geoff Richards, Davos (CH); Lolo Ap Gwynn, Aberystwyth (GB)

(73) Assignees: Dr. h. c. Roberts Mathys Stiftung, Bettlach (CH); AO Research Institute, Davos (CH)

( * ) Notice: Subject to any disclaimer, the term of this patent is extended or adjusted under 35 U.S.C. 154(b) by 780 days.

(21) Appl. No.: 10/581,270

(22) PCT Filed: Dec. 1, 2004

(86) PCT No.: PCT/EP2004/013649
§ 371 (c)(1),
(2), (4) Date: Apr. 25, 2007

(87) PCT Pub. No.: WO2005/053578
PCT Pub. Date: Jun. 16, 2005

(65) Prior Publication Data
US 2007/0282455 A1    Dec. 6, 2007

(30) Foreign Application Priority Data

Dec. 2, 2003  (EP) .................................. 03027740

(51) Int. Cl.
*A61F 2/28* (2006.01)
(52) U.S. Cl. ............... 623/23.72; 623/23.51; 623/23.56; 623/23.58
(58) Field of Classification Search ............... 623/23.72, 623/23.51, 23.56, 23.58
See application file for complete search history.

(56) References Cited

U.S. PATENT DOCUMENTS

| | | | |
|---|---|---|---|
| 5,141,510 A * | 8/1992 | Takagi et al. | 623/23.56 |
| 5,624,463 A | 4/1997 | Stone et al. | 623/18 |
| 5,658,343 A | 8/1997 | Häuselmann et al. | 623/20 |
| 6,319,712 B1 | 11/2001 | Meenen et al. | 435/395 |
| 6,447,701 B1 | 9/2002 | Heschel et al. | 264/28 |
| 6,626,950 B2 * | 9/2003 | Brown et al. | 623/23.72 |
| 6,656,489 B1 | 12/2003 | Mahmood et al. | 424/426 |
| 6,783,776 B2 * | 8/2004 | Spievack | 424/558 |
| 2003/0004578 A1 | 1/2003 | Brown et al. | 623/23.72 |
| 2003/0181978 A1 | 9/2003 | Brown et al. | 623/11.11 |
| 2007/0244484 A1 | 10/2007 | Luginbuehl | 606/86 |

FOREIGN PATENT DOCUMENTS

| | | |
|---|---|---|
| EP | 0562862 | 9/1993 |
| EP | 0677297 | 10/1995 |
| EP | 1064958 | 1/2001 |
| EP | 1275405 A | 1/2003 |

(Continued)

OTHER PUBLICATIONS

I. AP Gwynn, S. Wafe, K. Ito and R.G. Richards, "Novel Aspects to the Structure of Rabbit Articular Cartilage". European Cells and Materials, vol. 4, 2002, pp. 18-29.

*Primary Examiner* — Bruce E Snow
*Assistant Examiner* — Melissa Hoban
(74) *Attorney, Agent, or Firm* — Fitzpatrick, Cella, Harper & Scinto

(57) ABSTRACT

A triphasic prosthetic device for repairing or replacing cartilage or cartilage-like tissue. The prosthetic device comprises a highly oriented hollow body component between a superficial random oriented polymer layer and a base component.

40 Claims, 4 Drawing Sheets

FOREIGN PATENT DOCUMENTS

Figure 1:
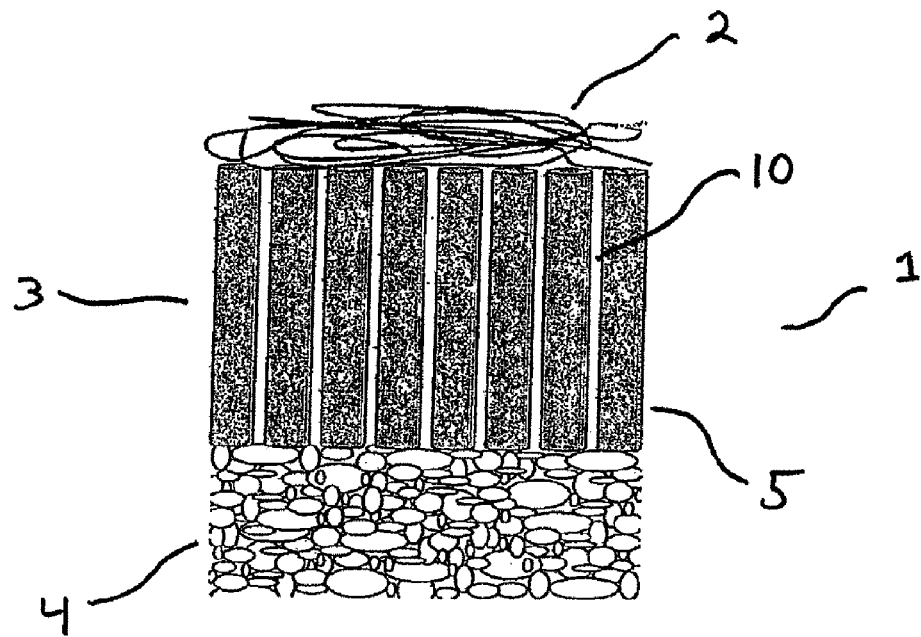

| | | |
|---|---|---|
| EP | 1277450 A2 | 1/2003 |
| JP | 01-299549 | 12/1989 |
| JP | 8-38524 | 2/1996 |
| JP | 11-267193 | 10/1999 |
| JP | 2000-237298 | 9/2000 |
| JP | 2003-102755 | 4/2003 |
| JP | 2007-526779 | 9/2007 |
| WO | WO91/08718 | 6/1991 |
| WO | WO01/85225 | 11/2001 |
| WO | WO02/07961 | 1/2002 |

* cited by examiner

PROSTHETIC DEVICE FOR CARTILAGE REPAIR

The present invention is directed to a triphasic prosthetic device for repairing or replacing cartilage or cartilage-like tissues. Said prosthetic devices are useful as articular cartilage substitution material and as scaffold for regeneration of articular cartilagenous tissues.

Articular cartilage tissue covers the ends of all bones that form diarthrodial joints. The resilient tissues provide the important characteristic of friction, lubrication, and wear in a joint. Furthermore, it acts as a shock absorber, distributing the load to the bones below. Without articular cartilage, stress and friction would occur to the extent that the joint would not permit motion. Articular cartilage has only a very limited capacity of regeneration. If this tissue is damaged or lost by traumatic events, or by chronic and progressive degeneration, it usually leads to painful arthrosis and decreased range of joint motion.

Recently, the structure of rabbit articular cartilage has been further elucidated in an article by I. ap Gwynn et al, European Cells and Materials, Vo. 4, pp. 18-29, 2002. The tibial articular cartilage has been shown to comprise a radial zone in which the aggrecan component of the extracellular matrix was arranged generally oriented in columns in the radial direction. As a terminating member a superficial zone, next to the tibial plateau, is provided and having a spongy collagen architecture.

Several methods have been established in the last decades for the treatment of injured and degenerated articular cartilage. Osteochondroal transplatation, microfracturing, heat treatment for sealing the surface, shaving, autologous chondrocyte transplantation (ACT), or total joint replacement are among the common techniques applied in today's orthopedic surgery.

Joint replacement techniques where metal, ceramic and/or plastic components are used to substitute partially or totally the damaged or degenerated joint have already a long and quite successful tradition. The use of allograft material has been successful to some extent for small transplants, however, good quality allografts are hardly available.

Osteochondroal transplantation (i.e. mosaicplasty) or autologous chondrocyte transplantation (ACT) are applied whenever total joint replacement is not yet indicated. These methods can be used to treat small and partial defects in a joint. In mosaicplasty defects are filled with osteochondral plugs harvested in non-load bearing areas. In ACT, chondrocytes are harvested by biopsy and grown in-vitro before a highly concentrated cell suspension is injected below an membrane (artificial or autologous) covering the defect area.

Commonly, the replacement of cartilage tissue with solid permanent artificial inserts has been unsatisfactorily because the opposing articular joint surface is damaged by unevenness or by the hardness of the inserts. Therefore, the transplantation technology had to take a step forward in the research of alternative cartilage materials such as biocompatible materials and structures for articular cartilage replacement.

For example, U.S. Pat. No. 5,624,463 describes a prosthetic articular cartilage device comprising a dry, porous volume matrix of biocompatible and at least bioresorbable fibres and a base component. Said matrix establishes a bioresorbable scaffold adapted for the ingrowth of articular chondrocytes and for supporting natural articulating joint forces. Useful fibres include collagen, reticulin, elastin, cellulose, alginic acid, chitosan or synthetic and biosynthetic analogs thereof. Fibres are ordered in substantially circumferentially extending or substantially radially extending orientations. The base component is provided as a support on which the fiber matrix is applied. It is configured to fit in a complementary aperture in defective bone to secure the position of such a device in the bone. The base component is a composite material comprising a dispersion of collagen and composition consisting of tricalcium phosphate and hydroxyapatite.

It has been shown, however, that the function of the above construction has not been always satisfactory. The reason is that said known prosthetic articular cartilage device is frequently unstable due to its structure and thus had to be replaced in the joint area by another surgical operation in to again repair cartilage joints such as knee and hip.

In view of this situation, in the field of articular cartilage replacement materials, there is a need for a structure suitable as a prosthetic articular cartilage which is made of natural resorbable materials or analogs thereof and having an improved structure stability and an accurate positioning in the bone. At the same time, the prosthetic device should be biomechanically able to withstand normal joint forces and to promote repair and replacement of cartilage tissue or cartilage-like tissue. These objects are solved by the prosthetic device according to claim 1.

The present invention relates to a prosthetic device for repairing or replacing cartilage or cartilage-like tissue which comprises a polymeric hollow body component 3, with a number of oriented hollow bodies, a base component 4 to anchor said polymeric hollow body component 3 in or onto an osteochondral environment and at least one superficial layer comprising randomly oriented fibres 2 provided on said polymeric hollow body component 3, wherein said number of highly oriented hollow bodies of the polymeric hollow body component 3 are aligned essentially in parallel to the insertion axis of the prosthetic device, i.e. perpendicularly to the plane of the articulating surface.

The subclaims concern preferred embodiments of the prosthetic device of the present invention.

It has been surprisingly found that the stability of a prosthetic articular cartilage device can be essentially improved by providing a polymeric hollow body component with a number of highly oriented hollow bodies 3 in such a way that the hollow bodies are aligned essentially in parallel to the insertion axis of the prosthetic device. The polymeric hollow body component is flanked by a base component and a superficial layer to form the triphasic structure of the device of the invention. The specific alignment of the hollow bodies in the layer perfectly mimics the cartilage and cartilage-like tissues providing an excellent mechanical stability. At the same time, a basis for rapid cartilage in-growth is provided, thus assuring a long term cartilage replacement.

Figure 2A:
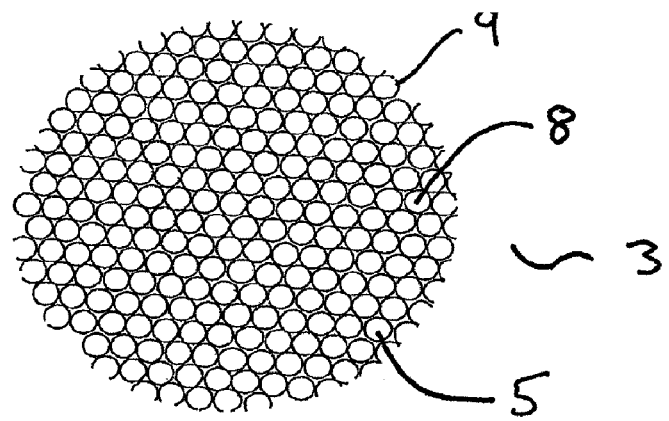
Figure 2B:
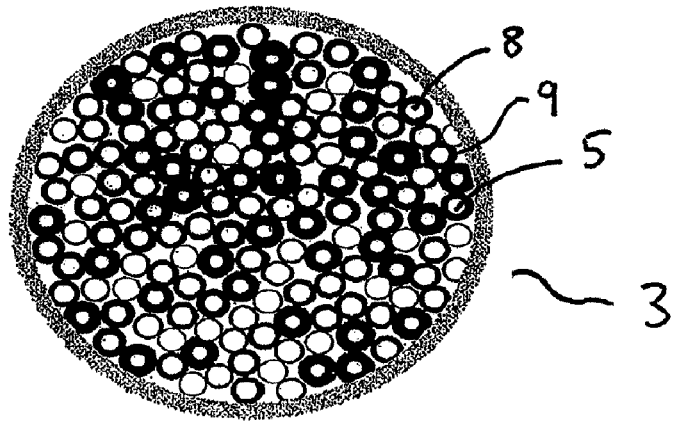
Figure 2C:
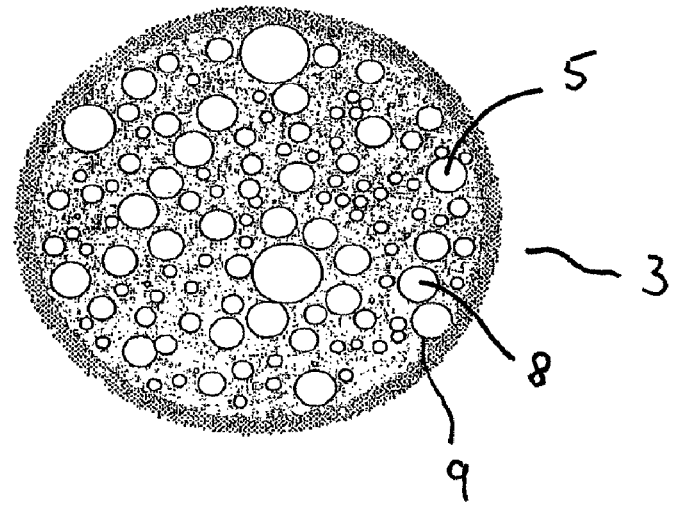
Figure 3:
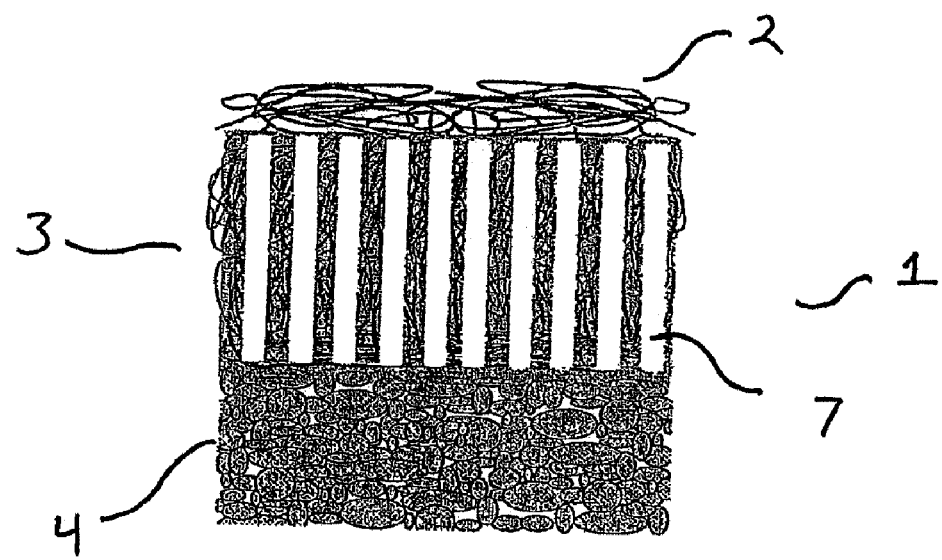
Figure 4:
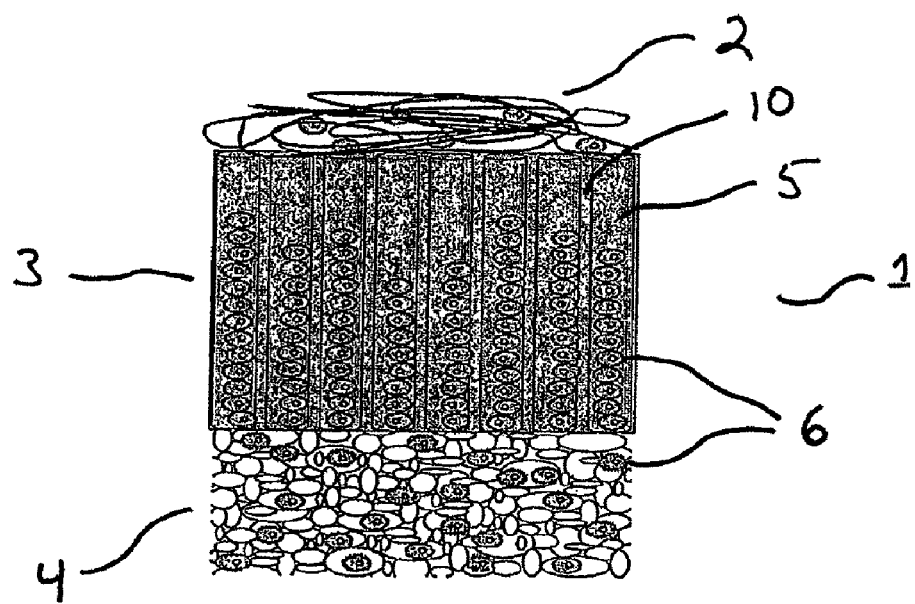

The invention itself may be more fully understood from the following description when read together with the accompanying Figures wherein FIG. 1 shows a vertical cross-sectional view of an embodiment of the prosthetic device of the invention;

FIGS. 2a, 2b, and 2c show a horizontal cross-section of the hollow bodies 5 of the polymeric hollow body component 3 in different packings and sizes;

FIG. 3 illustrates a vertical cross section of an embodiment of the device of the invention where physically/mechanically produced channels 7 are incorporated in solid polymer components 3 and FIG. 4 is a vertical cross-section of another embodiment of the device of the invention wherein cells are seeded with at least one externally added component 6 in components 2, 3 and 4.

FIG. 1 depicts a cross-section of the preferred form of a prosthetic device 1 embodying the invention. The device 1 includes at least one superficial layer comprising randomly oriented fibres of the biocompatible and/or at least partially resorbable material 2, a polymeric hollow body component 3, and a base component of a bone substitute material 4.

In principle, any materials can be used for the construction of the device of the invention as long as they are biocompatible. Preferably all materials are biodegradable. In one of the preferred embodiment of the invention the hollow body component 3 and the random fibres component 2 include synthetic polymers or molecules, natural polymers or molecules, biotechnologically derived polymers or molecules, biomacromolecules, or any combination thereof, while the base component 4 is based on a calcium phosphate material.

As can be seen from FIG. 1, the hollow bodies 5 of the polymeric hollow body component 3 are essentially aligned in a direction perpendicular to a top surface of the base component 4, which top surface faces the hollow bodies. The hollow bodies thus form a brush-like structure in a direction perpendicular to the base component 4.

The hollow bodies can be aligned to more than 50% in a direction perpendicular to the top surface of the base component 4. An alignment of more than 90% in a direction perpendicular to the base component 4 is preferred, more than 95% alignment is particularly preferred. The hollow bodies may change alignment direction and self-organize at the uppermost end of the brush like structure. This might occur under pressure after implantation.

The material to be used for the hollow bodies of the hollow body component 3 of the device of the invention is not particularly restricted to specific materials provided, however, the materials are bio-compatible. Preferably, a bio-degradable solid polymer is used which can be of any shape with the proviso that a channel may be provided therein. More preferably, a strange-like solid polymer is used, e.g. made by extrusion. Once the solid polymer has the desired shape, hollow spaces such as channels are formed therein by mechanical, physical and/or chemical methods. Examples for such methods are casting, drilling, etching, etc. which are well known to the person skilled in the art.

For some reason, it may be suitable that the solid polymer is porous. Porosity of the polymer may be provided during manufacturing the polymer.

Preferably, in the device of the invention, the inner channel diameter 8 of the hollow bodies of the polymeric hollow body component 3 is in range of 500 nm to 500 µm, with a preferred range of 5 µm to 150 nm.

The hollow bodies of component 3 of the device 1 of the invention usually have a wall thickness 9 ranging between 1 nm and 500 µm, a wall thickness being between 100 nm and 250 µm is preferred.

The hollow bodies themselves should usually have a height of 50 µm to 10 mm. A height between 100 µm to 2 mm is particularly preferred.

Specifically, the device of the present invention comprises a polymeric hollow body component which is formed by an assembly of oriented tubes. In this case, the space between the assembled tubes 10 is empty or filled with a substance selected from at least one synthetic polymer, natural polymer, biologically engineered polymer, or molecules thereof, biomicromolecules, or any combination thereof.

FIGS. 2a, 2b and 2c depict in different cross-sections some possible arrangements of the hollow bodies 5 of component 3. With respect to the lateral distribution of the hollow bodies of component 3, any type of distribution is possible, such as a homogenous or random distribution or a distribution in a specific pattern. Furthermore, the diameter of the hollow bodies and the wall thickness can be homogenous or variable within a hollow body component 3.

FIG. 3 depicts a second preferred form of a prosthetic device 1 embodying the invention. It may be suitable to use a solid or porous block of polymer with manufactured channels 7 as hollow body component 3. There are different methods to create these channels, well-known to persons skilled in the art. Techniques may include erosion, drilling, etching, form casting etc. Again, channel diameter, and distribution may be homogenous or variable.

It may be suitable to engineer the component 3 from molecules that self-assemble forming tube like hollow body structures to the final polymeric component 3. For stabilization reasons, such structures can be crosslinked.

In principle, any material can be used for the fibres of the superficial layer 2 which are randomly oriented to form three-dimensional structures of any kind as long as they are biocompatible. In order to enhance the stability of the structure 2, it may be that at least a fraction of material of the fibres is cross-linked. In one preferred embodiment of the invention the fibres 2 include synthetic polymers, natural polymers, biologically engineered polymers, the molecules thereof, biomacromolecules and any combination thereof.

The fibres of the superficial layer 2 themselves are not limited to any structure. They may be straight, twisted, curled, or of any tertiary structure. It is also possible to use a combination thereof. Additionally, the fibres themselves can be linear, branched or grafted.

The fibres of the superficial layer 2 may be constituted out of single polymer molecules, or out of assemblies of many molecules.

According to the invention, the shape and character of the fibres of the superficial layer 2 can be homogeneous or comprise a combination of various fibres previously mentioned different forms, including chemical, physical composition, and origin. The fibres can form a compact or loose random network, or an at least partially oriented assembly. The fibre-to-fibre distance can be varied within a broad range, i.e. between 1 nm to 1 mm, with a preferred fibre-to-fibre distance of 1 nanometer to 100 micrometers. The distances themselves can be homogeneous or heterogeneous. Examples of heterogeneous distances are gradient-like distributions, or random distributions, or specific pattern alignment, or any combination thereof.

The fibres of the superficial layer 2 of the device of the present invention can be provided as mono-filament or multi-filament fibres of any length. Fiber arrangement in a woven, non-woven twisted, knitted, or any combination thereof is possible. If desired, the lateral cross-section of the fibres 2 can be solid or hollow.

According to the invention, the fiber diameter may be varied in a broad range. Advantageously, a range of 50 nm to 1 mm is proposed. Preferably, the fiber diameter is in range of 1 µm to 250 µm.

It has been shown that one layer of fibres of the superficial layer 2 already brings about good results. However, in some instances, it can be advisable to provide a couple of layers of fibres which is, of course, dependent on the final use of the device of the invention 1. The assembly of multiple layer structures can be a head-head, head-tail, or tail-tail, and any combination thereof. It can also be an intercalated assembly wherein the clear interface border is lost between the different layers and gets continuous.

The superficial layer 2 usually has a thickness of 1 nm to 5 mm. It is preferred that the thickness is in a range of 10 µm to 2 mm. In some instances, however, that layer 2 can be missing and the hollow body component 3 is directly exposed at the surface.

Some specific indications require that the superficial layer 2 is added separately to the device or intra-operatively, only after implantation of the device. In this case the superficial layer 2 may be either in the form of a solid thin fibrous membrane or formed by adding a gelating liquid containing fibrous polymer.

In case of using mineral based materials for the fibre layer 2 and/or the hollow body component 3, a selection may be made from synthetic or natural materials with a glass-like structure, crystalline structure, or any combination thereof.

According to the invention, the fibres of the superficial layer 2 and the hollow bodies of the component 3 may have a flexible structure or a rigid structure depending on the final use of the device 1. In case of adapting to the articulation of a joint or opposing tissue, the fibres 2 should form a flexible structure.

The fiber material is usually homogeneous. Depending on the final use of the device of the invention 1, the fiber material can also be heterogeneous, i.e., selected from various materials or it can comprise an engineered combination of the materials as mentioned above.

In some instances, however, the fibres 2 and/or the hollow bodies of component 3 can be coated or grafted with one or more of the previously mentioned materials.

The device of the present invention 1 comprises, as a further essential structural component, a base component 4. The function of the base component 4 is to anchor the polymeric hollow body component 3 in or onto an osteochondral environment. This osteochondral anchor function helps to keep the device 1 in place when implanted. The base component 4 can be of variable size and shape. Preferably, the shape of the base component 4 is round cylindrical or conical. The diameter of the base component 4 can vary in stepwise manner or in a continuous transition zone of any size. In practice, the diameter is related to the defect size and ranges between 4 and 20 mm, with a total height being 1 to 30 mm. Preferably, the diameter is in a range of 4 and 20 mm, with a height being between 1 to 10 mm. The top surface of the base component 4 is usually either flat or it mimics the contour of the subchondral plate or the cartilage surface to be replaced.

The material of the base component 4 of the device of the invention 1 can be a material, which is normally used as a bone substitute. Examples of the material are those as listed above in connection with the material of the fibres of the superficial layer 2. If desired, the material for the base component 4 is a mineral material such as synthetic ceramic. The ceramic can be selected out of one or several of the following groups: calcium phosphates, calcium sulphates, calcium carbonates and any mixture thereof.

If the base component 4 of the device 1 is a calcium phosphate, one or more of the following composition groups is preferred: dicalcium phosphate dihydrate ($CaHPO_4 \times 2H_2O$), dicalcium phosphate ($CaHPO_4$), alpha-tricalcium phosphate (alpha-$Ca_3(PO_4)_2$), beta-tricalcium phosphate (beta-$Ca_3(PO_4)_2$), calcium deficient hydroxyl apatite ($Ca_9(PO_4)_5(HPO_4)OH$), hydroxyl apatite ($Ca_{10}(PO_4)_6OH_2$), carbonated apatite ($Ca_{10}(PO_4)_3(CO_3)_3$) ($OH)_2$), fluoroapatite ($Ca_{10}(PO_4)_6(F,OH)_2$), chloroapatite ($Ca_{10}(PO_4)_6(Cl,OH)_2$), whitlockite ($(Ca,Mg)_3(PO_4)_2$), tetracalcium phosphate ($Ca_4(PO_4)_2O$), oxyapatite ($Ca_{10}(PO_4)_6O$), beta-calcium pyrophosphate (beta-$Ca_2(P_2O_7)$), alpha-calcium pyrophosphate, gamma-calcium pyrophosphate, octacalcium phosphate ($Ca_8H_2(PO_4)_6 \times 5H_2O$).

It is also possible to have the above mentioned mineral materials doped or mixed with metallic, semi-metallic and/or non-metallic components, preferably magnesium, silicon, sodium, potassium, strontium and/or lithium.

In another preferred embodiment of the invention, the material of the base component 4 is a composite material comprising at least two different components. Examples of such composite materials are those comprising a mineral, inorganic, organic, biological, and/or biotechnological derived non-crystalline component and a mineral crystalline component. The non-crystalline components are often of polymeric nature.

In a preferred embodiment of the invention, the structure of the materials of the base component 4 is highly porous with interconnecting pores. This would allow any substances and cell in the subchondral environment to diffuse or migrate, respectively, into the base component 4.

In various forms of the invention, at least one of components 2, 3 and 4 has a liquid absorbing capacity by interactions with a solvent. Preferably, the liquid absorbing capacity is in a range of 0.1 to 99.9%, a range of 20.0 to 95.0% being particularly preferred.

Usually, the liquid to be absorbed is water and/or body fluid available at the position where the device 1 is implanted. When absorbing water and/or body fluids, the fibres 2 advantageously form a gel or transform to a gel-like state.

Upon uptake of water and/or body fluids the components can swell and, therefore, an internal pressure within the fiber component is built up. That pressure helps stabilizing the structure. Furthermore, externally added components including cells are entrapped under the pressure within the fiber structure as in a natural cartilage.

If desired, the device 1 of the invention may comprise a cell barrier layer between the polymeric hollow body component 3 and the base component 4. This layer acts as a barrier for cells and blood to prevent diffusion from the base component 4 into the polymeric hollow body component 3. It is, however, also possible to provide a barrier layer that is porous and/or has specific pores to allow selective or non-selective cells to pass through.

The interface between random fibre layer 2 and the hollow body component 3, and the hollow body component 3 and the base component 4 respectively, can be formed in various ways. It can be either a chemical, or a physical, or mechanical interaction, or any combination thereof that forms the stabilization zones comprising at least one layer. The stabilization zones can be either formed by material used for device components 2, 3, or 4, or by externally added components, and any combination thereof.

In another preferred embodiment of the device of the invention 1 as illustrated in FIG. 4, at least one externally added component 6 is included in any of the components. Usually said components are dispersed throughout component 2 and/or component 4 and/or component 3. Said components can be cells of different origin. The function is to support the generation of cartilage material and to enhance to improve healing, integration and mechanical properties of the device 1.

The cells are preferably autologous cells, allogenous cells, xenogenous cells, transfected cells and/or genetically engineered cells and mixtures thereof.

Particularly preferred cells, which can be present throughout the polymeric hollow body component 3 and the fibre layer of 2 are chondrocytes, chondral progenitor cells, pluripotent stem cells, tutipotent stem cells or combinations thereof. Examples for cells included in the base component 4 are osteoblasts, osteo-progenitor cells, pluripotent stem cells, tutipotent stem cells and combinations thereof. In some instances it can be desired to include blood or any fraction thereof in the base component 4.

Examples for another internally added components are pharmaceutical compounds including growth factors, engineered peptide-sequences, or antibiotics.

An example for another internally added components are gelating compounds including proteins, glycoaminoglycanes, carbohydrates, or polyethyleneoxides. These components can be added as free components, or they can be immobilized within the device of claim 1 by chemical, physical, or entrapment methods to prevent the washing-out.

The polymeric components of the device of the invention may be cross-linked.

The device of the present invention can be directly implanted in a defect, diseased, or deceased cartilaginous area such as articulating joints in humans and animals. Examples of these articulating joints are the cartilage areas in hip, elbow, and knee joints. Usually, implanting the device into a joint is made by surgical procedures. For example the insertion procedure can be as following:

In a first step, the defect area is cleaned and an osteochondral plug is removed with a chisel. Special equipment allows for exacting bottom and walls with regard to depths and widths. The prosthetic device of the invention is carefully pressed into position in such a manner that the upper edge of the base component 4 is on the same level with the calcified zone dividing the cartilage and the bone. The top surface of the fiber layer 2 should equal the height of the surrounding cartilage. Height differences may be exacted.

The operation can be either carried out in an open or in an arthroscopic manner.

As mentioned above and depicted in FIG. 4, the device of the invention can be seeded with cells and other externally added substances. There are different procedure possible. One of the procedures includes the harvesting of cells prior to the effective operational procedure. After purification and treatment of the harvested cells, they can be seeded either directly into the device 1 for in-vitro cultivation, or subsequent to a short or extended in-vitro expansion and cultivation step, all according to methods established in the art.

An other preferred procedure bypasses extensive in-vitro cultivation and is carried out as an intra-operative procedure. For that, cells are harvested during the operational procedure from the patient, purified and treated according to the methods established in the art. These cells are then seeded into the device 1, and device 1 is immediately implanted into the defect site.

For special applications, it will be also possible to assemble the device of the invention intra-operatively. I.e. the base component 4 is implanted first, and subsequently the hollow body component 3 is immobilized on to the base component 4. The height of the hollow body component 3 is adjusted to the contour of the joint after the immobilization procedure e.g. by shaving or heat treatment. Finally, at least one superficial layer 2 is provided onto the hollow body component 3.

The present invention is illustrated by means of the following examples.

EXAMPLES

Example 1

A prosthetic device is engineered from a porous interconnected cylindrical beta-tri-calcium-phosphate body of sizing 5 mm in diameter and 10 mm in height, as a subchondral anchor, and a 4 mm layer of a degradable polyurethane above. The polyurethane layer embodies vertical oriented hollow bodies of a diameter of 60 micrometer in a random lateral arrangement with a mean center-to-center distance of the hollow bodies of 100 micrometer. The hollow bodies in the polymer layer are produced in a casting process. The resulting prosthetic device is an ideal implant for cartilage repair.

A properly sized tubular chisel is introduced perpendicular to the defect site in the joint. In a first step in the implantation, the chisel is tapped into cartilage and the osseous base, slightly larger than the defect (1-3 mm larger) at the defect site. The defect size is exacted regarding depth and diameter to the specific dimensions of the prosthetic device. Subsequently, the anchor of the graft is soaked in a saline solution before the prosthetic device is inserted through the universal guide tool. No additional fixation of the prosthetic device is necessary due to the exact fit. Then, the surface of the prosthetic device is resurfaced—if necessary—to match the exact curvature of the joint surface and the height of the surrounding articular surface. Finally autologous chondrocytes are filled into the hollow bodies in the polymer layer and a fibrous permeable polyurethane membrane is placed above the hollow bodies to prevent the cells coming out and to prevent the tubes filling with blood clots and before the wound site is closed.

Example 2

A prosthetic device is engineered from a porous interconnected cylindrical hydroxy apatite body of sizing 8 mm in diameter and 15 mm in height, as subchondral anchor, and a 8 mm layer of poly hydroxy methacrylate (PHEMA) with random arranged hollow bodies of diameters ranging between 10 and 50 micrometers. These vertical oriented tube like hollow bodies in the pHEMA layer are obtained casting the polymer into an appropriate form. The resulting prosthetic device is an ideal implant for cartilage repair.

In a first step, the defect site is cleaned of frayed cartilagenous tissue and it is adjusted to the size of the prosthetic device. A properly sized tubular chisel is introduced perpendicular to the defect site in the joint. The chisel is tapped into cartilage and the osseous base of the defect site. The defect size is exacted regarding depth and diameter to the specific dimensions of the prosthetic device. Subsequently, harvested bone marrow stromal cells are added to the ceramic anchor. Next, the prosthetic device is inserted through the universal guide tool. No additional fixation of the prosthetic device is necessary due to the exact fit and the swelling of the fiber layer. Finally, the surface of the prosthetic device is resurfaced—if necessary—to match the exact curvature of the joint surface and the height of the surrounding articular surface.

Example 3

A prosthetic device is engineered from a porous interconnected cylindrical beta-tri-calcium-phosphate and calcium sulfate composite body sizing 12 mm in diameter and 10 mm in height, as subchondral anchor, and a 6 mm polymer layer consisting of mixture of hollow polycaprolactone (PCL) filaments and polyethylenoxid (PEO) filaments. The inner diameter of the hollow filaments ranges between 10 and 80 micrometer. The PEO filaments have typically a diameter of 1 to 20 micrometer. The lateral distribution and arrangement of the hollow filaments is random, the space between the hollow fibers is filled with the PEO material. The polymer structure is stabilized by chemical crosslinking. The polymer layer is immobilized on the ceramic anchor by a melt process. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Bone marrow stromal cells and platelet rich plasma is added to the anchor, and the prosthetic device is inserted subsequently by the universal guide tool. No additional fixation of the prosthetic device is necessary due to the exact fit. If necessary, the surface of the prosthetic device is finally resurfaced to match the exact curvature of the joint surface and the height of the surrounding articular surface. Finally, adult stem cells and cells of a chondrogenic phenotype are mixed in a specific ratio and applied onto the polymer layer. A fibrous gelating matrix is used to seal the hollow bodies.

Example 4

A prosthetic device is engineered from a porous interconnected cylindrical beta-tri-calcium-phosphate body sizing 30 mm in diameter and 25 mm in height with a convex surface curvature, as subchondral anchor, and a 6 mm layer of degradable Pluronic polymer with vertical tube like hollow bodies that have a random lateral arrangement. The diameter of the hollow bodies is variable, ranging between 5 and 150 micrometer. The ceramic anchor and the polymer layer are fused together by a cement reaction. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Chondrocytes and mesemchymal progenitor cells are harvested by a biopsy intra-operatively and prepared for immediate application onto the polymer layer. Platelet rich plasma is added to the anchor, and the prosthetic device is inserted subsequently by the universal guide tool. No additional fixation of the prosthetic device is necessary due to the exact fit. The surface of the prosthetic device is finally resurfaced to match the exact curvature of the joint surface and the height of the surrounding articular surface. The hollow bodies are sealed with a thin layer of fibrous polymer.

Example 5

A prosthetic device is engineered from a porous interconnected cylindrical beta-tri-calcium-phosphate body sizing 8 mm in diameter and 10 mm in height, as subchrondral anchor, and a 3 mm layer of alginate polymer. Vertical hollow bodies of 50 micrometer diameter in the alginate polymer are formed while casting the polymer on top of the ceramic anchor. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Bone marrow stromal cells are added to the anchor and the prosthetic device is inserted subsequently by the universal guide tool. No additional fixation of the prosthetic device is necessary due to the exact fit of the anchor. Additionally, the device is stabilized by the swelling of the polymer layer after in-vitro cultivated cells of chondrogenic phenotype are added. If necessary, the surface of the prosthetic device is finally resurfaced to match the exact curvature of the joint surface and the height of the surrounding articular surface.

Example 6

A prosthetic device is engineered from a porous interconnected cylindrical calcium deficient hydroxy apatite (CDHA) body sizing 4 mm in diameter and 5 mm in height, as subchondral anchor and a 3 mm layer of a chitosan fibers mesh with vertical oriented hollow bodies that exhibit diameters ranging between 20 and 100 micrometers. The hollow bodies were created by laser drilling in random lateral arrangement. The polymer layer is grafted onto a ceramic layer that acts as a selective barrier between the polymer layer and the anchor. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Bone marrow stromal cells are added to the anchor, and the prosthetic device is inserted subsequently by the universal guide tool. No additional fixation of the prosthetic device is necessary due to the exact fit. If necessary, the surface of the prosthetic device is finally resurfaced to match the exact curvature of the joint surface and the height of the surrounding articular surface. Finally, intra-operatively harvested and isolated mesenchymal progenitor cells are applied onto the polymer layer and the top is sealed with a thin fibrous membrane or gel-like fibrous matrix.

Example 7

A prosthetic device is engineered from a porous interconnected cylindrical beta-tri-calcium-phosphate body sizing 10 mm in diameter and 10 mm in height, as subchondral anchor and a 3 mm layer of copolymer polylacticacid/polycaprolactone (PLA/PCL). Vertical tube like hollow bodies have diameters ranging between 30 and 300 micrometer and are drilled mechanically prior to graft the polymer layer onto the ceramic anchor. The hollow bodies are arranged according to a well-defined pattern. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Bone marrow stromal cells are added to the anchor, and the prosthetic device is inserted subsequently by the universal guide tool. No additional fixation of the prosthetic device is necessary due to the exact fit. If necessary, the surface of the prosthetic device is finally resurfaced to match the exact curvature of the joint surface and the height of the surrounding articular surface. Finally, in-vitro cultivated autologous cells of a chondrogenic phenotype are applied in a fibrous gelating matrix as cell suspension to the polymer layer.

Example 8

A prosthetic device is engineered from a porous interconnected cylindrical calcium deficient hydroxy apatite body sizing 4 mm in diameter and 5 mm in height, as subchondral anchor, and a 2 mm layer of hollow PCL filaments, intermixed with hyaluronic acid and collagen that also form the cover layer. The hollow filaments are vertically arranged and have an inner open diameter of 60 micrometer. The lateral arrangement is randomly and the polymer construct is stabilized by crosslinking of the polymers. The polymer layer is embedded in a ceramic layer that acts as a selective barrier between the fiber layer and the anchor. The resulting prosthetic device is an ideal implant for cartilage repair.

Autologous chondrocytes are added to layer and the device is pre-cultivated in-vitro. For implantation, a properly sized tubular chisel is introduced perpendicular to the defect site in the joint. The chisel is tapped into cartilage and the osseous base of the defect site. The defect size is exacted regarding depth and diameter to the specific dimensions of the prosthetic device. Platelet Rich Plasma is added to the anchor, and the prosthetic device is inserted subsequently by the special guide tool.

Example 9

A prosthetic device is engineered of textile polymer sheet with vertically arranged hollow bodies of a mean diameter of 100 micrometer. The polymer sheet with its hollow bodies is created by state-of-the-art textile technology out of PCL/PLA filaments. The hollow bodies are created by ultrathin woven fiber textiles. The prosthetic device assembly is carried intra-operative according to the following procedure.

For implantation, the defect site is exacted with the help of a chisel is tapped into cartilage and the osseous base of the defect site. The polymer textile sheet with its hollow bodies is cut into appropriate size. The prosthetic device anchoring is achieved by applying a calcium phosphate based cement into the subchondral space. Subsequently, the cut textile is placed on top of the cement, which will immobilize it upon hardening. A dense polymer layer at bottom side of the textile prevents the filling up of the hollow bodies with cement. The height of the polymer layer is adjusted to the surrounding cartilage by shaving the polymer and pressing into the cement anchor. Finally, intra-operatively harvested and isolated chondrocytes and progenitor cells are mixed with a gelating matrix and applied to the textile containing the hollow bodies. The fibrous gelating matrix is also used to seal the hollow bodies by a random oriented fibrous layer. The operational procedure may be carried out as open surgery or as arthroscopy in minimal invasive manner.

The invention claimed is:

1. A triphasic prosthetic device for repairing or replacing cartilage or cartilage like-tissue (1) comprising:
    a polymeric hollow body component (3) with a number of highly oriented hollow bodies;
    a base component (4) comprising a bone substitute material that is a synthetic ceramic to anchor said polymeric hollow body component (3) in or onto an osteochondral environment; and
    at least one superficial layer comprising randomly oriented fibres (2) provided on said polymeric hollow body component (3)
    wherein more than 50% of said number of highly oriented hollow bodies of the polymeric hollow body component (3) are aligned essentially parallel to the insertion axis of the prosthetic device (1).

2. The device according to claim 1, wherein more then 90% of said hollow bodies are aligned perpendicular to the plane of the articulating surface.

3. The device according to claim 1, wherein an inner channel diameter of the hollow bodies of polymeric hollow body component (3) is in a range of 500 nm to 500 µm.

4. The device according to claim 3, wherein the inner channels have a wall thickness ranging between 1 nm and 500 µm.

5. The device according to claim 4, wherein the wall thickness is between 100 nm and 250 µm.

6. The device according to claim 3, wherein said inner channel diameter is in a range of 5 µm to 150 µm.

7. The device according to claim 1, wherein the polymeric hollow body component (3) is formed by an assembly of oriented tubes.

8. The device according to claim 7, wherein a space between the assembled tubes is empty or filled with a substance selected from the group consisting of synthetic polymers, natural polymers, biologically engineered polymers, molecules thereof, biomacromolecules and any combination thereof.

9. The device according to claim 1, wherein the hollow body component is a solid block of polymer with channels.

10. The device according to claim 9, wherein the channels are formed by at least one of mechanical, physical and chemical methods in a solid polymer.

11. The device according to claim 10, wherein said solid polymer is porous.

12. The device according to claim 1, wherein lateral distribution of the hollow bodies of component (3) is homogenous, random or in a specific pattern.

13. The device according to claim 1, wherein said hollow bodies of the hollow body component (3) have a height of 50 µm to 10 mm.

14. The device according to claim 13, wherein the height is between 100 µm and 2 mm.

15. The device according to claim 1, wherein said synthetic ceramic comprises at least one of calcium phosphate, calcium sulfate and calcium carbonate.

16. The device according to claim 15, wherein said calcium phosphate is selected from the group consisting of dicalcium phosphate dihydrate ($CaHPO_4 \times 2H_2O$), dicalcium phosphate ($CaHPO_4$), alpha-tricalcium phosphate (alpha-$Ca_3(PO_4)_2$), beta-tricalcium phosphate (beta-$Ca_3(PO_4)_2$), calcium deficient hydroxyl apatite ($Ca_9(PO_4)_5(HPO_4)OH$), hydroxyl apatite ($Ca_9(PO_4)_6OH_2$), carbonated apatite ($Ca_{10}(PO_4)_3(CO_3)_3)(OH)_2$) fluoroapatite ($Ca_{10}(PO_4)_6(F,OH)_2$) chloroapatite ($Ca_{10}(PO_4)_6 (Cl, OH)_2$), whitlockite (($Ca,Mg)_3(PO_4)_2$), tetracalcium phosphate ($Ca_4(PO_4)_2O$), oxyapatite ($Ca_{10}(PO_4)_6O$), beta-calcium pyrophosphate (beta-$Ca_2(P_2O_7)$), alpha-calcium pyrophosphate, gamma-calcium pyrophosphate, octacalcium phosphate ($Ca_8H_2(PO_4)_6 \times 5H_2O$) and mixtures thereof.

17. The device according to claim 1, wherein said synthetic ceramic comprises at least one of metallic, semimetallic components and non-metallic components, preferably magnesium, silicon, sodium, potassium, strontium and lithium.

18. The device according to claim 1, wherein the material is a composite material comprising at least two different components.

19. The device according to claim 1, wherein more than 95% of said hollow bodies are aligned perpendicular to the plane of the articulating surface.

20. The device according to claim 1, wherein the shape of the base component (4) is round cylindrical or conical.

21. The device according to claim 20, wherein the diameter of the base component (4) ranges between 4 and 20 mm, with a height being 1 to 30 mm.

22. The device according to claim 21, wherein the diameter of the base component (4) ranges between 4 and 20 mm, with a height being between 1 to 10 mm.

23. The device according to claim 22, wherein said superficial layer (2) is missing, or formed by uppermost end of the hollow body component.

24. The device according to claim 1, wherein said superficial layer (2) has a thickness of 1 nm to 5 mm.

25. The device according to claim 24, wherein said thickness is in the range of 10 µm to 2 mm.

26. The device according to claim 1, wherein at least one of the randomly oriented fibers (2), the polymeric hollow body component (3) and the base component (4) has a liquid absorbing capacity in a range of 0.1% to 99.9%.

27. The device according to claim 26, wherein said liquid absorbing capacity is in a range of 20.0 to 95.0%.

28. The device according to claim 26, wherein the liquid is at least one of an aqueous media and a body fluid.

29. The device according to claim 1, wherein the polymeric hollow body component is cross-linked.

30. The device according to claim 1, further comprising at least one externally added component.

31. The device according to claim 30, wherein said externally added components are cells of different origin.

32. The device according to claim 31, wherein said cells are at least one of autologous cells, allogenous cells, xenogenous cells, transfected cells and genetically engineered cells.

33. The device according to claim 30, wherein chondrocytes, chondral progenitor cells, pluripotent cells, tutipotent cells or combinations thereof are present throughout at least one of the randomly oriented fibers (2) and the polymeric hollow body component (3).

34. The device according to claim 30, wherein osteoplasts, osteo-progenitor cells, pluripotent stem cells, tutipotent stem cells or combinations thereof are present throughout the base component (4).

35. The device according to claim 30, wherein blood or any fraction thereof is present throughout the base component (4).

36. The device according to claim 30, wherein pharmaceutical compounds are contained.

37. A device according to claim 1, wherein a cell barrier layer is additionally provided between said polymeric hollow body component (3) and said base component (4).

38. A device according to claim 37, wherein the cell barrier layer is a cell selective barrier layer.

39. A use of the device according to claim 1 for implantation in articulating joints in humans and animals.

40. The use according to claim 39 for regeneration of articulator cartilagenous tissue.

* * * * *